US010188557B2

(12) United States Patent
Hundorf et al.

(10) Patent No.: US 10,188,557 B2
(45) Date of Patent: Jan. 29, 2019

(54) APPARATUS AND PROCESS FOR TRANSFERRING SUBSTRATE MATERIAL AND PARTICULATE MATERIAL

(75) Inventors: Harald Hermann Hundorf, Bonn (DE); Marion Hundorf, legal representative, Bonn (DE); Peter Ostle, Euskirchen (DE); Siegfried Link, Euskirchen (DE); Martin Dohmen, Euskirchen (DE)

(73) Assignee: The Procter & Gamble Company, Cincinnati, OH (US)

( * ) Notice: Subject to any disclaimer, the term of this patent is extended or adjusted under 35 U.S.C. 154(b) by 1587 days.

(21) Appl. No.: 13/191,726

(22) Filed: Jul. 27, 2011

(65) Prior Publication Data
US 2012/0024470 A1 Feb. 2, 2012

(30) Foreign Application Priority Data
Jul. 27, 2010 (EP) .................................. 10170895

(51) Int. Cl.
*A61F 13/15* (2006.01)

(52) U.S. Cl.
CPC ... *A61F 13/15658* (2013.01); *Y10T 156/1052* (2015.01)

(58) Field of Classification Search
CPC .......... A61F 13/15658; A61F 13/15764; A61F 13/5323; B05C 1/0804
USPC ....... 156/390, 297, 446, 470, 538–540, 556, 156/582
See application file for complete search history.

(56) References Cited

U.S. PATENT DOCUMENTS

| 5,562,646 | A | 10/1996 | Goldman et al. |
| 5,964,974 | A * | 10/1999 | Hinton .......................... 156/215 |
| 6,706,129 | B2 * | 3/2004 | Ando et al. ................... 156/62.2 |
| 8,137,746 | B2 | 3/2012 | Schmidt et al. |
| 2001/0006089 | A1 | 7/2001 | Ando et al. |
| 2006/0021695 | A1 * | 2/2006 | Blessing et al. .............. 156/196 |
| 2006/0048880 | A1 | 3/2006 | Blessing et al. |

FOREIGN PATENT DOCUMENTS

| EP | 0 691 133 A | 1/1996 |
| EP | 1 621 166 A1 | 2/2006 |
| JP | 2002/272782 A | 9/2002 |
| JP | 2008/237449 A | 10/2008 |
| WO | WO 2006/014854 | 2/2006 |

OTHER PUBLICATIONS

PCT International Search Report dated Oct. 6, 2011, 9 pages.

* cited by examiner

*Primary Examiner* — Christopher T Schatz
(74) *Attorney, Agent, or Firm* — Charles R. Matson; Abbey A. Lopez; Richard L. Alexander

(57) ABSTRACT

An apparatus for transferring, at high speed and in a very effective and accurate and cost effective manner, particulate material from a first moving endless surface with reservoir (s) to a second moving endless surface carrying a substrate material, such as a nonwoven web material, and transferring said combination of substrate material with particulate material to a further apparatus unit; said second moving endless surface is adjacent and in communication with a first and a second vacuum chamber, with different vacuum pressures and/or different size. Also a process is provided, using the described apparatus.

10 Claims, 3 Drawing Sheets

APPARATUS AND PROCESS FOR TRANSFERRING SUBSTRATE MATERIAL AND PARTICULATE MATERIAL

CROSS REFERENCE TO RELATED APPLICATIONS

This application claims priority to EP 10170895.6, filed Jul. 27, 2010, which is hereby incorporated by reference in its entirety.

FIELD OF THE INVENTION

This invention relates to an apparatus for transferring, at high speed and in an accurate and cost effective manner, particulate material from a first moving endless surface with reservoir(s) to a second moving endless surface carrying a substrate material, such as a nonwoven web material, and transferring (to a further processing unit/step), said combination of substrate material with particulate material, said second moving endless surface being adjacent and in communication with a first and a second vacuum chamber, with different vacuum pressures and/or different size. The invention also relates to a specific process, e.g. using the apparatus described herein

BACKGROUND TO THE INVENTION

Traditionally, absorbent articles such as diapers comprise an absorbent core with water-absorbent (cellulose) fibers and particles of superabsorbent polymer particle, also referred to as particles of absorbent gelling material or AGM, enclosed by a substrate material, or supported by a substrate material and then closed by a further material, e.g. such as a nonwoven.

Absorbent articles with so-called profiled absorbent cores have been developed, whereby certain regions of the article comprise more AGM than other regions. In such instances, accurate deposition of AGM is important to obtain the required profile. Furthermore, in the case of absorbent cores with only small amounts of, or no, cellulose fibers (having thus AGM particles as the only liquid storage material) accurate AGM distribution is highly important.

Various approaches have been proposed for obtaining absorbent cores with primarily AGM particles and for obtaining absorbent cores that have AGM particles in a specific profile or distribution, such as a predetermined pattern, MD-, CD- and/or thickness-profile. These approaches include indirect printing methods, whereby the AGM particles are taken up by a first surface, e.g. a drum surface, from a bulk storage of AGM particles—said drum surface having reservoirs, the number, size and position of which determines the amount and pattern of AGM granules taken up by the drum- and whereby the drum then rotates towards a substrate such as a nonwoven, to then release the AGM onto the substrate, for example carried by a moving surface, such as the surface of a further drum. For example, WO2006/014854 describes such a process.

The inventors found that such proposed indirect printing processes are in some instances difficult to run at high speed, for example at speeds of 800 ppm or more, or 1000 ppm or more (parts (absorbent structures) per minute), and/or when fine particulate material is used and/or when small (and large quantities of) reservoirs are used for printing. It has been found that at high speeds, the particulate material is not always accurately transferred onto the substrate material, resulting in for example dust creation, incorrect print of a specific profile etc. The inventors found that it may be beneficial to apply a strong vacuum to the substrate material to ensure better deposition of the particulate material onto the substrate.

However, the inventors found that with the prior art proposed apparatus it not always possible to maintain sufficient vacuum in a (cost) effective manner during the transfer of the substrate material with particulate material (for example to a further processing step) of the substrate with the AGM, in particular when running the apparatus at high speed. The inventors have now found an improved apparatus and process for depositing particulate material onto a substrate in an accurate manner and cost effective manner, even at high speed and/or even when fine particulate material is present, and/or even when very small quantities are transferred per surface area.

SUMMARY OF THE INVENTION

The invention relates to an apparatus (1) for making a structure that comprises a combination of a particulate material (100) and a substrate material (110), including:
a) a first moving endless surface (40) with a direction of movement (MD) and with one or more reservoirs (50), said first moving endless surface (40) and reservoirs (50) thereof being for transferring particulate material (100) to:
b) a second moving endless surface (200) with a direction of movement (MD) carrying a substrate material (110) for receiving said particulate material (100) from said first moving endless surface (40) in a receiving zone and for transferring said combination of said particulate material and said substrate material in a transferring zone, e.g. to a further apparatus unit, said second moving endless surface moving/being in said receiving zone adjacent a first vacuum chamber (210) and being in gas communication therewith, and said second moving endless surface moving/being in said transferring zone adjacent a second vacuum chamber (220), and being in gas communication therewith, said receiving zone and said transferring zone being adjacent (in MD) one another,
whereby the ratio of the said negative vacuum pressure in said first vacuum chamber (210) to the negative vacuum pressure in said second vacuum chamber (220) is at least 4:3, or for example at least 5:3 or at least 2:1 and for example up to 10:1.
The apparatus thus typically also comprises a further apparatus unit, adjacent said second moving endless surface, and beyond said transfer zone.

The invention also relates to an apparatus with a) and b) as above, but whereby the first vacuum chamber (210) has adjacent said second moving endless surface a first surface area with a first open area and said second vacuum chamber (220) has adjacent said second moving endless surface a second surface area with a second open area, and the ratio of the first open area to the second open area is 3:4 or less, or 2:3 or less, or 1:2 or less, or 1:3 or less.

The invention also relates to a apparatus with a) and b) as above, whereby the ratio of the said negative vacuum pressure in said first vacuum chamber (210) to the negative vacuum pressure in said second vacuum chamber (220) is at least 4:3, or for example at least 5:3 or at least 2:1 and for example up to 10:1, and whereby said ratio of the first open area to the second open area is 3:4 or less, or 2:3 or less, or 1:2 or less, or 1:3 or less.

The second moving endless surface is for example a cylindrical rotating surface, rotating around a second stationary (cylindrical) stator (230); the combination of such a surface and stator is also referred to as drum. The stator (230) may contain for example said first vacuum chamber and said second vacuum chamber.

The inventors found that the specific selection of the high(er) vacuum forces (so very low(er) negative vacuum pressures) in the receiving zone, when the particulate material is deposited onto the substrate, and then the relatively reduced vacuum forces during transfer can improve the exact deposition of the particulate material onto the substrate (e.g. in the desired pattern) in a very accurate and effective manner. Furthermore, this apparatus and process of the invention can achieve this in a particular cost effective manner, because only a small section of the second moving endless surface in the receiving zone needs to be adjacent a vacuum chamber with (expensive) large negative vacuum pressures, whilst the transferring zone can be adjacent a vacuum chamber with only relatively reduced negative vacuum pressures.

The invention also relates to a process for making a structure that comprises a combination of particulate material (100) and a substrate material (110), using the apparatus (1) as described herein; and/or a process for making a structure comprising a combination of a substrate material (110) and a particulate material (100) the step of:
a) depositing with a first endless moving surface (40) comprising one or more reservoirs (50) particulate material (100), contained by said reservoir(s), onto a substrate material (110), carried by a second moving endless surface (200) to form a combination of a substrate material and particulate material, in a receiving zone of said second moving endless surface; and providing simultaneously a first negative vacuum pressure in said receiving zone;
b) transferring said combination of said substrate material and particulate material, through a transferring zone of said second endless moving surface, and simultaneously providing a second negative vacuum pressure in said receiving zone, (typically to a further processing step),
whereby the ratio of said first negative vacuum pressure to said second negative vacuum pressure is at least 4:3, as further described herein below.

The particulate material may be particulate absorbent material and the apparatus and process herein may be to make an absorbent structure, e.g. absorbent core, useful in (disposable) absorbent articles, such as feminine hygiene article and diapers or adult incontinent products.

DETAILED DESCRIPTION OF THE INVENTION

Particulate Material

Figure 1:
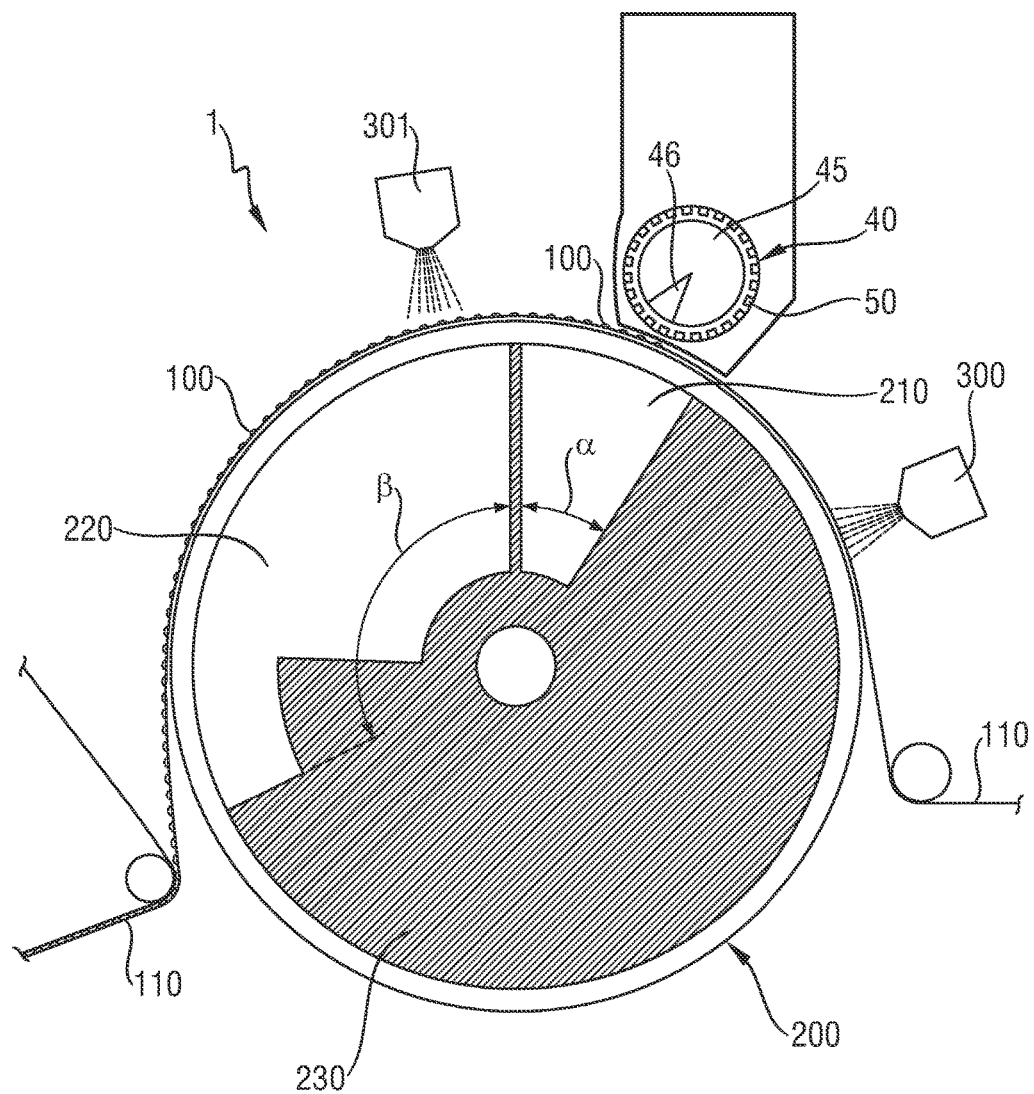
FIG. 1 shows a cross sectional side view (cross section taken along MD and along the direction perpendicular thereto) of a portion of an exemplary apparatus (1) of the invention.

The particulate material (100) herein may be any material in particulate form, e.g. flowable in dry state, which includes particles, flakes, fibers, spheres, agglomerated particles and other forms known in the art. The particulate material as used herein may also be a two or more different material, e.g. in different form, different chemistry. The particulate material as used herein may for example be a mixture of particles and fibers.

In one embodiment herein, the particulate material (100) comprises or is particulate absorbent (or: superabsorbent) material. This material is typically polymeric material, such as known as particulate absorbent gelling material, herein referred to as AGM. This refers to polymeric materials in particulate form that can absorb at least 10 times their weight of a 0.9% saline solution, i.e. having a CRC value of at least 10 g/g as measured using the Centrifuge Retention Capacity test of EDANA (European Disposables and Nonwovens Association), test method No. 441.2-02 "Centrifuge retention capacity". The particulate AGM herein may have a high sorption capacity, e.g. having a CRC of for example at least 20 g/g, or at 30 g/g. Upper limits may for example be up to 150 g/g, or up to 100 g/g.

The particulate AGM may have a good permeability for liquid, for example, having a SFC value of at least $10 \times 10^{-7}$ cm$^3$ s/g; or preferably at least $30 \times 10^{-7}$ cm$^3$·s/g, or at least $50 \times 10^{-7}$ cm$^3$ s/g $10 \times 10^{-7}$ cm$^3$s/g, or possibly permeability SFC value of at least $100 \times 10^{-7}$ cm$^3$s/g, or at least a SFC of $120 \times 10^{-7}$ cm$^3$sec/g. This SFC is a measure of permeability and an indication of porosity is provided by the saline flow conductivity of the gel bed as described in U.S. Pat. No. 5,562,646, (Goldman et al.) issued Oct. 8, 1996 (whereby however a 0.9% NaCl solution is used instead of Jayco solution). Upper limits may for example be up to 350 or up to 250 ($\times 10^{-7}$ cm$^3$·s/g).

In one embodiment herein the polymers of said AGM are internally cross-linked and/or surface crosslinked polymers.

In one embodiment herein, the particulate material herein is absorbent material comprising or consisting of particles of polyacrylic acids/polyacrylate polymers, for example having a neutralization degree of from 60% to 90%, or about 75%, having for example sodium counter ions, as known in the art, e.g. surface crosslinked and/or internally crosslinked polyacrylic acid/polyacrylate polymers.

In one embodiment herein, the particulate material (100) is in the form of particles with, a mass medium particle size up to 2 mm, or for example between 50 microns and 2 mm or to 1 mm, or preferably from 100 or 200 or 300 or 400 or 500 μm, or to 1000 or to 800 or to 700 μm; as can for example be measured by the method set out in for example EP-A-0691133. In one embodiment of the invention, the particulate material (100) is in the form of particles with at least 80% by weight of the particles having a particle size between 50 μm and 1200 μm and a mass median particle size between any of the preferred range combinations above. In yet another or additional embodiment of the invention the particulate material (100) has a relatively narrow range of particle sizes, e.g. with the majority (e.g. at least 80% by weight or preferably at least 90% or even at least 95%) of particles having a particle size between 50 μm and 1000 μm, preferably between 100 μm and 800 μm, and more preferably between 200 μm and 600 μm.

In addition, or in another embodiment of the invention, said particles are essentially spherical.

The particulate material (100) herein may advantageously comprise less than 15% by weight of water, or less than 10%, or less than 8% or less than 5%. The water-content can be determined by the Edana test, number ERT 430.1-99 (February 1999) which involves drying the particulate material (100) at 105° Celsius for 3 hours and determining the moisture content by the weight loss of the particulate material (100) after drying.

The particulate AGM herein may be particles of AGM that are surface coated or surface treated (this not including surface-crosslinking, which may be an additional surface-treatment); such coatings and surface treatment steps are well known in the art, and include surface treatment with one or more inorganic powders, including silicates, phosphates, and coatings of polymeric material, including elastomeric polymeric materials, or film-forming polymeric materials.

Substrate Material (110)

The (e.g. absorbent) structure producible with the apparatus (1) and method of the invention comprises a combination of a substrate material and the particulate material (100). This substrate material may be any material, for example in sheet form; the substrate material may be web material; the substrate material may for example be paper (e.g. sheet/web), film (e.g. sheet/web), woven (e.g. sheet/web) or nonwoven (e.g. sheet/web); or combinations thereof. The substrate material may be a laminate (e.g. sheet/web), for example of a laminate of two or more nonwoven layers, or two or more film layers, or one or more nonwoven layers and one or more film layers.

In one embodiment herein, the substrate material comprises or is a nonwoven, e.g. a nonwoven web; nonwoven, when used herein, refers to a manufactured sheet or web of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled.

The fibers of the nonwoven may be of natural or man-made origin and may be staple or continuous filaments or be formed in situ. Commercially available fibers come in several different forms: short fibers (known as staple, or chopped), continuous single fibers (filaments or monofilaments), untwisted bundles of continuous filaments (tow), and twisted bundles of continuous filaments (yarn). The fibers may be bicomponent fibers, for example having a sheet-core arrangement, e.g. with different polymers forming the sheet and the core. Nonwoven fabrics can be formed by many processes such as meltblowing, spunbonding, solvent spinning, electrospinning, and carding. The basis weight of nonwoven fabrics is usually expressed in grams per square meter (gsm).

The nonwoven herein may be made of hydrophilic fibers; "Hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The substrate material herein may be air-permeable. Films useful herein may therefore comprise micro pores. The substrate material may have for example an air-permeability of from 40 or from 50, to 300 or to 200 $m^3/(m^2 \times min)$, as determined by EDANA method 140-1-99 (125 Pa, 38.3 $cm^2$). The substrate material may alternatively have a lower air-permeability, e.g. being non-air-permeable, to for example be better detained on a moving surface comprising vacuum.

The substrate material may be a nonwoven material, e.g. a nonwoven web or nonwoven laminate web comprising two or more nonwoven layers laminated to one another, for example of the SMS or SMMS type.

The substrate material may have a CD-extensibility or a MD-extensibility, for example of more the 20%, or for example more than 100%, but for example not more than 200%. The ratio of MD-extensibility to the CD-extensibility is at a given load not more than one to two.

Further exemplary structures are described herein below.

Apparatus (1)

First Moving Endless Surface (40)

The apparatus (1) herein has a first moving endless surface (40); this may be any moving surface that can rotate to provide a moving endless surface, for example it may be a transporter belt or a cylindrical surface, such as of a drum, as known in the art, which can rotate and thus provide an endless surface.

The first moving endless surface (40) comprises one or more reservoirs (50), for containing a particulate material, as described above, and for depositing it from said reservoir(s) onto a substrate material (110).

The first and second (described herein after) moving endless surfaces herein have each a direction of movement of said surface, e.g. said rotating surface, herein referred to as Machine direction, MD. "Direction of movement or MD" is herein to be taken to be the direction of movement in a certain point of said surface or the average direction of movement in a certain specified area of said surface, as specified herein. Thus, for a curved, e.g. cylindrical moving endless surface (40), the direction of movement in a certain point of the surface, or the average direction of movement of a certain area of said surface, is herein determined by determining the tangent in said point or the average tangent of an area (then, said tangent being the average direction of movement in said area).

The direction of the surface perpendicular to MD is herein referred to as Cross machine direction, CD (MD and CD being in the plane of the surface).

The first moving endless surface (40) is typically a rotating surface that rotates around a stationary element, for example cylindrical surface rotating around a (e.g. cylindrical) stator (45), that may for example comprise one or more vacuum chambers and/or one or more air chambers (46), also together referred to as drum. The stationary element (e.g. stator (45)) and the combination of the stationary element (e.g. stator) and the rotating first surface (40) have each a certain radius. Each radius may for example depend on what structure is produced, and what size of structure is produced, and for example how many structures are produced per cycle of the first moving endless surface (40), e.g. drum. For example, the first cylindrical moving surface and/or the first stator (45) may have a radius of at least 40 mm, or of at least 50 mm; it may be for example up to 300 mm, or up to 200 mm.

The first moving endless surface (40) may have any suitable width (in CD), but for example a width corresponding (substantially) to the width of the structure to be produced; this for example may be at least 40 mm, or at least 60 mm, or for example up to 400 mm, or up to 200 mm.

It may be useful that the first moving endless surface (40) has opposing lateral zones and a central zone therein between, extending along the whole surface in MD, and said reservoir(s) (50) are only present in said central zone. Then, the width dimensions of the surface may apply to the width of the central zone instead.

It should be understood that for purpose of determination of properties of the first moving endless surface (40), such as the MD, the radius, the width of said first moving endless surface (40), the surface area where no reservoir(s) (50) are present (e.g. the area between reservoirs (50)) is used for such determinations. This surface area between reservoirs (50) is herein referred to as "outer surface area" of said first moving endless surface (40).

The reservoir or reservoirs (50) may have any dimensions and shape, including cubical, rectangular, cylindrical, semispherical, conical, or any other shape. The first moving endless surface (40) typically comprises reservoir(s) (50) with a void volume that can be filled with particulate material(s) (100). This may be a single reservoir. However, it may be preferred that there are two or more, e.g. a multitude of reservoirs. This multitude may be any suitable number of reservoirs, but for example at least 20 or at least 50.

The reservoirs (50) may be present as identical reservoirs (50), or they may vary in dimension(s) or shape. They may be present in a pattern over (and protruding into) the surface of said first moving endless surface (40). The exact reservoir (50) pattern, dimensions etc. will depend on the required structure to be formed, but may for example also depend on the particle size of the particulate material (100), process speed etc. In one embodiment at least 30% of the surface area of the first moving endless surface (40) or of said central zone thereof, described above comprises said reservoirs (50), preferably at least 40% or at least 50%.

The reservoirs (50) may be present as lines of reservoirs (50) in MD and rows in CD. Alternatively, they reservoirs (50) may for example be present in so-called alternating rows and/or lines (whereby alternating reservoirs (50) form a row and/or line). Said lines may extend substantially parallel to, and equally spaced from, one another and/or said rows may extend substantially parallel to, and equally spaced from, one another.

The distance in MD between the centre point of a reservoir (50) (said centre point being in the plane of the outer surface of the first moving endless surface (40)) and the centre point of a neighboring reservoir (50) (in a line of reservoirs (50)) may for example be at least 2 mm, or at least 4 mm, or at least 6 mm, or for example up to 40 mm or up to 30 mm or up to 20 mm. This may apply to all such distances between neighboring reservoirs (50) in MD, or this may be an average over all such distances.

The distance in CD between the centre point of a reservoir (50) (said centre point being in the plane of the outer surface of the first moving endless surface (40)) and the centre point of a neighboring reservoir (50) (in a row of reservoirs (50)) may for example also be as above.

In one embodiment, the MD dimension (which may be the diameter) of a reservoir (50) may be (on average over all reservoirs (50) and/or for each reservoir (measured over the outer surface of the first moving endless surface (40)) at least 1 mm, or at least 2 mm, or at least 4 mm, and for example at the most 20 mm or at the most 15 mm. The CD dimension may be within the same ranges as above, or it may even be the same as the MD dimensions for one or more or each reservoir.

The reservoirs (50) may have any suitable dept dimension, and it may depend for example on the height of the first moving endless surface (40) (e.g. radius), the thickness/caliper of the desired structure to be produced, the particle size of the material, etc. The maximum depth of a reservoir (50) and/or of all reservoirs (50), and/or the average maximum depth (average over all maximum depths of all reservoirs (50)) may for example be at least 1 mm, or at least 1.5 mm, or for example 2 mm or more, and for example up to 20 mm, or up to 15 mm, or in some embodiment herein, up to 10 mm, or to 5 mm or to 4 mm or to mm.

The first moving endless surface (40) may be adjacent a hopper comprising said particulate material, and it may rotate past the hopper, to receive the particulate material in the reservoir(s) and to transfer it (by rotation). One possibility to hold the particulate material(s) (100) in the reservoirs (50) may be a vacuum applied to the inner side of the first moving endless surface (40) in combination with suction holes in (the bottom) of the reservoirs (50), to thus apply the vacuum suction onto the particulate material. This can be done by providing one or more vacuum chambers adjacent the surface, e.g. in the first stator (45) and/or optionally one or more vacuum chambers joined to said stator (but not comprised by the stator), that are in gas (air) communication with said surface. The vacuum is for example released just before or at the point (typically being a CD extending area) where the particulate material is transferred to the second moving endless surface (e.g. the receiving zone of said second moving endless surface), e.g. the point where the first moving endless surface (40) is adjacent and in close proximity to said second moving endless surface (200). Additional air pressure may then be applied to said particulate material (100) to ensure that the material flows from the reservoir(s) (50) to the second moving endless surface (200). The first stator (45) may thus comprise a gas (air)-chamber (46) (at about (and just beyond) said CD-extending area where the particles need to be transferred to the substrate material) with positive pressure that is in gas (air)-communication with said reservoir(s), to blow the particulate material from the reservoirs onto said substrate material (110) carried onto the second endless moving surface (200), as for example shown in FIG. 1. Alternatively, or in addition, the apparatus may have gas (air) chamber(s) with positive pressure, joined to the stator, but not comprised by the stator, that are in gas (air) communication with said surface.

Second Moving Endless Surface (200)

The second moving endless surface (200), carrying a substrate material (110) receives the particulate material in a receiving zone. The second moving endless surface (200) (and said substrate material) is in said receiving zone adjacent a first vacuum chamber (210).

The second moving endless surface carries the combination of the substrate material and particulate material to and through a transferring zone, typically to a further apparatus unit/process step (described herein after). The second moving endless surface (200) and said substrate material with particulate material are in said receiving zone adjacent a second vacuum chamber (220).

In the apparatus (1) and process of the invention, the receiving zone of said apparatus can be define by the presence of the first vacuum chamber or a first vacuum pressure, adjacent the second moving endless surface; the transferring zone can be defined by the presence of a second vacuum chamber or a second (e.g. lower) vacuum pressure, adjacent the second moving endless surface, and adjacent, in MD the first vacuum chamber.

The second moving endless surface may be in any suitable form provided it can rotate, such as a belt, or for example the second moving endless surface may be cylindrical. This is for example shown in FIG. 1.

Figure 2:
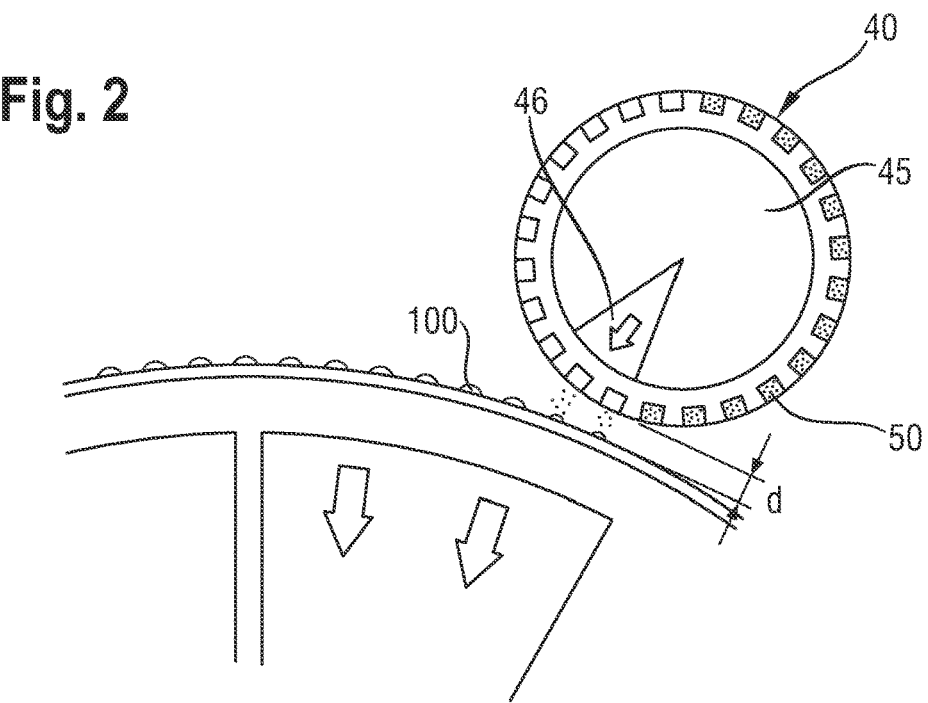
FIG. 2 shows an enlarged partial view of the cross sectional view of FIG. 1.

The closest proximity point (e.g. typically this being a line, extending in CD; this line/point is shown in for example shown in FIG. 2) between the first moving endless surface (40) and said second moving endless surface (200) is typically in said receiving zone; the distance (d) between said first moving endless surface and said second moving endless surface in said proximity point may for example be between 0.5 mm and 30 mm, or for example between 1 mm, or 2 mm, and up to 20 mm, or up to 15 mm.

In some embodiments herein, the second moving endless surface (200) is a rotating surface that rotates around a stationary element, for example a stator that comprises said first and second vacuum chambers (210, 220) (also referred to as drum). The second surface (200) may be cylindrical, and said second stationary element (stator 230) may be cylindrical.

The stationary element (e.g. stator (230)) and/or the combination of the stationary element (e.g. stator) and the rotating surface with one or more reservoirs have each a certain radius. Each radius may for example depend on what structure is produced, and what size of structure is produced, and for example the process speed.

For example, the combination of said cylindrical second rotating surface (200) and stator (e.g. drum) may have a radius of at least 80 mm, or of at least 100 mm; it may be for example up to 1000 mm, or up to 600 mm.

The ratios of the radius of the first moving endless surface and/or of the radius of the first stator, to the radius of the second moving endless surface and/or the radius of the second stator may (each individual or all) may for example be 2:3 or less, or for example 1:2 or less, for example 1:3 or less, or for example at least 1:10.

The second moving endless surface (200) carries said substrate material typically only over part of that surface at any point of time. For example, if it is cylindrical surface said second moving endless surface (200) is a rotating endless surface, is may only carry said substrate material over up to 300°, or up to 270° or up to 200°, but typically at least 60°, or at least 90°.

For a second moving endless surface that has a cylindrical circumference, the receiving zone may form/be present over for example at least 3°, or at least 5°, and/or for example up to 60°, or for example up to 45° or up to 30° or up to 20° (of the circle of rotation, hence in MD-shown as angle α in FIG. 1).

The transferring zone may form/be present over for example at least 20°, or at least 30°, and/or for example up to 270° or for example up to 200° or up to 150° or up to 120° (of the circle of rotation, hence in MD-shown as angle β in FIG. 1).

In some embodiments herein, the first vacuum chamber may have the same or a larger MD dimension than the second vacuum chamber, provided the vacuum pressure ratios herein are met. In some embodiments of the apparatus or process of the invention, and in particular for process accuracy and/or cost efficiency, said first vacuum chamber has a MD dimension L1 defined by a first angle (α) and said second vacuum chamber has a MD dimension L2 defined by a second angle (β) and the ratio of α to β is 3:4 or less, or for example 2:3 or less, or 1:2 or less or 1:3 or less. The first moving surface may be positioned substantially above the second moving endless surface, to allow gravity to aid deposition of the particulate material(s) onto the substrate material. Thereto, the first moving endless surface may for example be positioned substantially above the second moving endless surface, at a position between the 270° (or 9 o'clock position) and 90° (or 3 o'clock position) of the rotating (circular) second moving endless surface, or for example at a position between the 300° or 315° and 60° or 45° (0° being on the line of gravity), as for example shown in the FIG. 1.

The second moving endless surface (200) may be any suitable surface that allows gas passage in order to apply a vacuum onto the substrate material carried thereon. It thereto has a certain total open area, typically a homogenous total open area in use. The second moving endless surface may thereto typically have openings in a supporting structure, such as for example: the surface may be a mesh surface with a open areas between the mesh material; it may be a grid formed by endless MD-extending bars and CD extending cross-bars with open areas therein between; hereby the MD extending bars may for example be (substantially) parallel to and (equally) spaced from one another; and/or the plurality of cross bars extending along the direction perpendicular to the direction of movement of said second moving endless surface may extend (substantially) parallel to and (equally) spaced from one another.

Typically, the structure or pattern of openings in said second moving endless surface is homogenous over its surface facing the vacuum chambers and/or over its opposing surface facing the substrate material. Furthermore, since the second moving endless surface moves with a high speed, as described herein after, the total open area can typically be considered homogeneous in use.

The first vacuum chamber (210) has adjacent said second moving endless surface and hence adjacent said substrate (110) a certain first surface area that is open, i.e. it has one or more openings so it can be in gas communication with said substrate material carried on said second moving endless surface, said opening or openings herein being referred to as a first open area of the first vacuum chamber.

(Since the second moving endless surface has in use a homogeneous total open area, as described above, the effect of the supporting structure such as the mesh material, cross bars etc. can for the purpose of this invention be neglected). This first open area is in the receiving zone in gas communication with said substrate material.

The first open area of the first vacuum chamber may for example be from 50 or 100 or 150 cm$^2$, to 400 or to 300 or to 250 cm$^2$.

The second vacuum chamber (220) has adjacent said second moving endless surface and hence adjacent said substrate (110) a certain second surface area that is open, i.e. it has one or more openings so it can be in gas communication with said substrate material carried on said second moving endless surface, said opening or openings herein being referred to as second open area of the second vacuum chamber. (Since the second moving endless surface has in use a homogeneous total open area, as described above, the effect of the supporting structure such as the mesh material, cross bars etc. can for the purpose of this invention be neglected). This second open area is in the transferring zone in gas communication with said substrate material.

The second open area of the second vacuum chamber is more than the open area of the first vacuum chamber, and it may for example be from 200 or 250 cm$^2$, to 1000, or to 700, or to 500 cm$^2$.

In some embodiments of the apparatus or process herein, the ratio of said first open area (of the first vacuum chamber) to said second open area (of the second vacuum chamber) is for example 2:3 or less, or 1:2 or less or 1:3 or less.

This first to second open area ratio and/or specific first and second areas may be beneficial to ensure a large negative vacuum pressure can be created in said first vacuum chamber without excessive energy consumption, whilst still ensuring accurate reception and transfer of the particulate material by the second moving endless surface.

Figure 4:
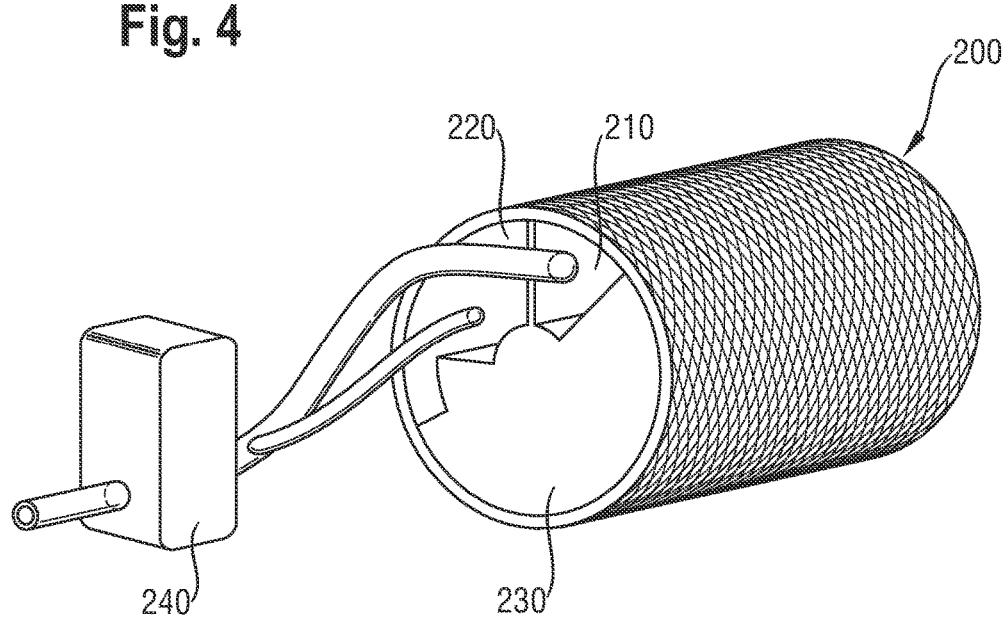
FIG. 4 shows perspective view of a part of an alternative exemplary apparatus of the invention, showing a second moving endless surface and a single vacuum fan.

The first vacuum chamber (210) and second vacuum chamber (220) may be connected to the same vacuum fan (240) that creates said negative vacuum pressure in said vacuum chambers; this fan is typically not present in said stator but for example in proximity to said second endless moving surface. This is for example shown in FIG. 4. The connection of said fan (240) to said second vacuum chamber may comprise a gas flow control device, to control the flow of gas and thus the vacuum pressures produced, according to the values described herein. The gas flow control device may be any device known in the art, such as a slide gate, butterfly valve. The connection from the fan (240) to the second vacuum chamber may also be restricted, to allow a reduced vacuum pressure to be established in said second vacuum chamber. The connection from said fan (240) to said second vacuum chamber may also be narrower than the connection from said fan to said first vacuum chamber, as for example shown in FIG. 4.

Figure 3:
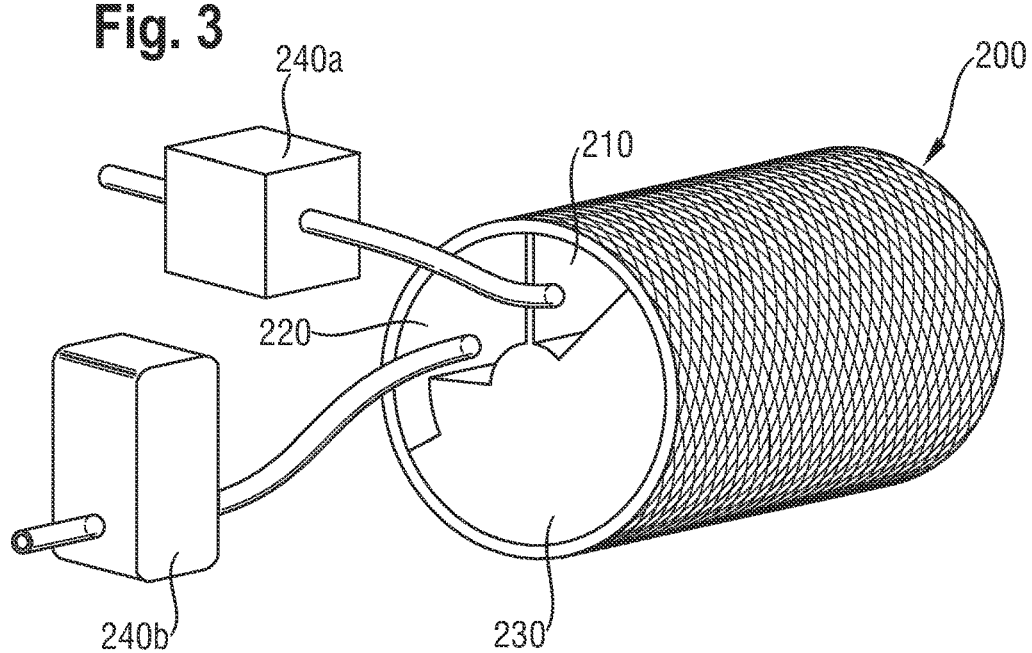
FIG. 3 shows perspective view of a part of an exemplary apparatus of the invention, showing a second moving endless surface and vacuum fans.

In other embodiments, and as for example shown in FIG. 3, the first vacuum chamber (210) is connected to a first vacuum fan (240*a*) and the second vacuum chamber (220) is connected to a second vacuum fan (240*b*) (that are not connected to one anther).

In some embodiment herein the first vacuum chamber may for example have a first negative vacuum pressure of −5 kPa or less, or −6.5 kPa or less, or −7.5 kPa or less, or for example from −6.5 kPa or from −7.5 kPa, to −20 kPa or to −15 kPa.

The second vacuum chamber has a smaller/reduced vacuum pressure compared to said first vacuum pressure, for example said second vacuum pressure in said second vacuum chamber being in the range from −0.5 kPa to −5 kPa, or to −4.5 kPa or to −4 kPa or to −3.5 kPa.

As mentioned above, in some embodiment herein, the ratio of said first negative vacuum pressure to said second negative vacuum pressure is at least 4:3, or as described herein above.

The vacuum pressure in the first chamber, and equally in the second chamber is measurable by placing a pressure sensor in a wall of the chamber, for example by placing the sensor in a side wall adjacent (and for example perpendicular to) the vacuum chamber side with the opening/openings of (that is adjacent the moving endless surface), but as far away as possible from said side.

This can be done with a sensor from BD Sensors (model DMP 331-110-M160-3-5-M00-300-1-000;
 −160-0 mbar; connected with Viton (FKM) seals).

The second moving endless surface (200) and substrate thereon may have the same surface speed as the first moving endless surface (40), or it may have a different surface speed. In one embodiment, the second moving endless surface and/or the first moving endless surface has a speed of at least 4.5 m/s, or at least 6 m/s, or at least 8 m/s or at least 10 m/s; when the process and apparatus is for the production of structures, such as absorbent cores, it may for example have a speed of at least 800 parts (structures) per minute or at least 1000 parts per minute.

After reception by said substrate material of said the particulate material (100), the combination of the substrate material and particulate material transfers in (and through) said transfer zone, for example to a further apparatus unit or process step. It should be understood that for the purpose of the invention, the transfer zone ends where the combination of the substrate and particulate material is no longer in gas communication with said second vacuum chamber (220), e.g. where said combination leaves the second moving endless surface. The process and apparatus herein typically transfer the combination of the substrate material and particulate material to a "further apparatus unit", or to a "further processing step". This further processing step/further apparatus unit is thus beyond (i.e. downstream) the transferring zone and beyond the second transferring vacuum chamber (220).

As for example shown in FIG. 1, the apparatus may comprise as further apparatus unit an anvil roll for receiving the combination of the substrate material and particulate material; the further apparatus unit/process step may be an apparatus unit/for or process step of receiving the combination of the substrate material and particulate material and receiving a further substrate material (optionally with particulate material) and combining said substrate materials, as shown in FIG. 1, and further described below; the further processing step/apparatus unit may be an apparatus unit for/process step of applying adhesive to said combination; it may be a further apparatus unit for/process step of cutting the combination of the substrate material and particulate material.

The apparatus/process herein may comprise "additional apparatus unit (s)/additional process step(s) that are placed or take place upstream from said first endless moving surface, or upstream from said receiving zone, or that may be placed/take place in the transferring zone. For example, the substrate material (110) may comprise (before deposition of the particulate material), an adhesive, in order to, at least partially, adhere the particulate material (100) to the substrate material (110). The adhesive may be applied in a pattern, whereby parts of the substrate (110) do not comprise adhesive and parts of the substrate (110) do comprises adhesive. The pattern may correspond to the pattern of the reservoirs (50) of the first moving endless surface (40). The apparatus herein may thus comprise as additional apparatus unit adhesive application unit (300) upstream from said first moving endless surface (40). The process herein may comprise as additional process step the application of an adhesive to the substrate prior to the reception of said particulate material thereon.

For example, in addition to the above or alternative, during the transfer of the combination of the substrate material and particulate material adhesive may be applied to said combination or only to said particulate material. The apparatus may thus comprise an additional adhesive application unit (301) downstream from the first moving endless surface, for example on the opposite side of the second moving endless surface to the second vacuum chamber in said transferring zone, and/or downstream from the transferring zone. The process herein may accordingly comprise additional process steps of applying adhesive to said substrate material and/or to said combination or to said particulate material in said transferring zone.

In the embodiment shown for example in FIG. 1, an optional additional upstream adhesive unit (300) applies an adhesive to the substrate material and am optional additional downstream adhesive unit (310) applies an adhesive to said combination of substrate material and particulate material in said receiving zone, whilst a further apparatus unit—downstream (beyond) the transferring zone; adjacent the second moving endless surface—such as an anvil roll, receives said combination and combines it with a further substrate material.

The further/additional adhesive application unit(s) may be selected from any type known in the art, in particular slot coating units and spray units.

The resulting combination of substrate material with particulate material may be a web and it may transfer to a cutting unit, (which may be the further unit herein) that cuts the substrate with particulate material into individual structures. In addition or alternatively, the substrate material with particulate material may move to a unit that folds the substrate material over the particulate material, The apparatus/process may have a subsequent unit/process step for sealing said folded substrate material or to seal the substrate material and further substrate material, to enclose the particulate material therein between. The sealing may be done by any means, for example by ultrasonic bonding, thermo-bonding or adhesive-bonding.

The adhesive that may be applied onto said particulate material, e.g. with the adhesive application unit shown as (310) in FIG. 1, may for example be a thermoplastic adhesive material that may serve to at least partially cover and at least partially immobilize the particulate material (100), for example a thermoplastic adhesive material in fibrous form, e.g. fibrous layer which is at least partially in contact with the particulate material (100) and optionally partially in contact with the substrate material (110). The thermoplastic material may be a hot melt adhesive material.

In certain embodiments, the thermoplastic (adhesive) material may be in the form of fibers of an average thickness of about 1 to about 50 micrometers or about 1 to about 35 micrometers and an average length of about 5 mm to about 50 mm or about 5 mm to about 30 mm.

The further substrate material may comprise the same material as the substrate material (110), or may comprise a different material. In certain embodiments, suitable materials for the further substrate material are the non-woven materials, useful for the substrate (110), described herein above. As mentioned herein, the further substrate material may comprise an adhesive material and/or particulate material.

Process

The invention also provides a process for making a structure that comprises a combination of particulate material (100) and a substrate material (110), using the apparatus (1) and option additional units as described herein.

Thus, all features and characteristics described herein above equally may apply the processes of the invention.

In some embodiments, the process for making a structure comprising a combination of a substrate material (110) and a particulate material (100) comprises the steps of:
  a) depositing with a first endless moving surface (40) comprising one or more reservoirs (50) comprising particulate material (100), contained by said reservoir(s), onto a substrate material (110), carried by a second moving endless surface (200) to form a combination of a substrate material and particulate material, in a receiving zone of said second moving endless surface; whilst providing (simultaneously) a first negative vacuum pressure in said receiving zone;
  b) transferring said combination of said substrate material and particulate material, through a transferring zone of said second endless moving surface, whilst providing (simultaneously) a second negative vacuum pressure in said receiving zone, and transferring this combination to a further processing step,
  whereby the ratio of said first negative vacuum pressure to said second negative vacuum pressure is at least 4:3, or as described herein.

The process may be done at the process speeds as described herein. It may be to make precursor absorbent structures or absorbents structures, for use in absorbent articles, such as sanitary napkins or diapers.

As mentioned above, the process may comprise the further process step selected from: applying a second, further substrate material (as described above), optionally being a combination thereof with a particulate material, to said combination of substrate material (110) and particulate material (100); folding said substrate material (110) over said particulate material (100); applying an adhesive to said combination of substrate material (110) and particulate material (100); cutting said combination of substrate material and particulate material; or combinations thereof.

Absorbent Cores and Absorbent Articles

The apparatus (1) and method of the invention are for example useful to produce (precursor) absorbent structures, such as (precursor) acquisition layers and/or absorbent cores for absorbent articles.

"Absorbent article" refers to devices that absorb and contain body exudates, and, more specifically, refers to devices that are placed against or in proximity to the body of the wearer to absorb and contain the various exudates discharged from the body. Absorbent articles may include diapers, including fastenable diapers and (refastenable) training pants; adult incontinence undergarments (pads, diapers) feminine hygiene products (sanitary napkins, pantyliners), breast pads, care mats, bibs, wound dressing products, and the like. "Diaper" refers to an absorbent article generally worn by infants and incontinent persons about the lower torso so as to encircle the waist and legs of the wearer and that is specifically adapted to receive and contain urinary and fecal matter. As used herein, the term "body fluids" or "body exudates" includes, but is not limited to, urine, blood, vaginal discharges, breast milk, sweat and fecal matter.

As well known in the art, the absorbent core is the portion of the article that retains absorbed bodily fluids. The absorbent core herein thus comprises the particulate material (100) that is an absorbent particulate material (100) (as defined herein) disposed on a substrate material (110), formed by the apparatus (1) and process herein. The absorbent core is typically sandwiched between at least a backsheet and a topsheet.

Preferred absorbent articles comprise a topsheet, facing the wearer in use, for example a nonwoven sheet, and/or an apertured sheet, including apertured formed films, as known in the art, and a backsheet, an absorbent core, having optionally a core coversheet facing the wearer in use. The backsheet may be liquid impervious, as known in the art. In preferred embodiments, the liquid impervious backsheet comprises a thin plastic film such as a thermoplastic film having a thickness of about 0.01 mm to about 0.05 mm. Suitable backsheet materials comprise typically breathable material, which permit vapors to escape from the diaper while still preventing exudates from passing through the backsheet. Suitable backsheet films include those manufactured by Tredegar Industries Inc. of Terre Haute, Ind. and sold under the trade names X15306, X10962 and X10964. The backsheet, or any portion thereof, may be elastically extendable in one or more directions. The backsheet may be attached or joined to a topsheet, the absorbent core, or any other element of the diaper by any attachment means known in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An apparatus for making a structure that comprises a combination of a particulate material and a substrate material, including:
   a) a first moving endless surface with a direction of movement (MD) and with one or more of reservoirs, said first moving endless surface and reservoirs thereof being for transferring particulate material to:
   b) a second moving endless surface with a direction of movement (MD) carrying a substrate material for receiving said particulate material from said first moving endless surface in a receiving zone and for transferring said combination of said particulate material and said substrate material in a transferring zone, said second moving endless surface being in said receiving zone adjacent a first vacuum chamber and being in gas communication therewith, and said second moving endless surface being in said transferring zone adjacent a second vacuum chamber, and being in gas communication therewith, said receiving zone and said transferring zone being adjacent (in MD) one another,
   c) an adhesive application unit for applying adhesive to said combination of said substrate and said particulate material, said adhesive application unit positioned downstream of said first moving endless surface opposite said second moving endless surface and said second vacuum chamber in said transferring zone;
      wherein the ratio of the said negative vacuum pressure in said first vacuum chamber to the negative vacuum pressure in said second vacuum chamber is at least 4:3; and
   d) an anvil roll downstream of said transferring zone for receiving said combination of said particulate material and said substrate material and combining said combination with a further substrate material.

2. An apparatus for making a structure that comprises a combination of a particulate material and a substrate material, including:
   a) a first moving endless surface with a direction of movement (MD) and with one or more of reservoirs, said first moving endless surface and reservoirs thereof being for transferring particulate material to:
   b) a second moving endless surface with a direction of movement (MD) carrying a substrate material for receiving said particulate material from said first moving endless surface in a receiving zone and for transferring said combination of said particulate material and said substrate material in a transferring zone, said second moving endless surface being in said receiving zone adjacent a first vacuum chamber and being in gas communication therewith, and said second moving endless surface being in said transferring zone adjacent a second vacuum chamber, and being in gas communication therewith, said receiving zone and said transferring zone being adjacent (in MD) one another,
   c) an adhesive application unit for applying adhesive to said combination of said substrate and said particulate material, said adhesive application unit positioned downstream of said first moving endless surface opposite said second moving endless surface and said second vacuum chamber in said transferring zone;
      wherein the first vacuum chamber has adjacent said second moving endless surface a first surface area with a first open area and said second vacuum chamber has adjacent said second moving endless surface a second surface area with a second open area, and the ratio of the first open area to the second open area is 3:4 or less; and
   d) an anvil roll downstream of said transferring zone for receiving said combination of said particulate material and said substrate material and combining said combination with a further substrate material.

3. The apparatus of claim 1, wherein said first moving endless surface is a cylindrical rotating endless surface, rotating around a first stator; and said second moving endless surface is a cylindrical rotating endless surface, rotating around a second stator and said first and second vacuum chambers are comprised by said second stator.

4. The apparatus of claim 2, wherein said first moving endless surface is a cylindrical rotating endless surface, rotating around a first stator; and said second moving endless surface is a cylindrical rotating endless surface, rotating around a second stator and said first and second vacuum chambers are comprised by said second stator.

5. The apparatus of claim 4, wherein said first moving endless surface has a plurality of reservoirs, and said first stator comprises an air chamber for containing pressurized air, and said air chamber being in air-communication with said plurality of reservoirs or part thereof to facilitate release of particulate material from said reservoir(s).

6. The apparatus of claim 1, wherein the closest proximity point (CD—extending line) between the first moving endless surface and said second moving endless surface is in said receiving zone and the distance (d) between said first moving endless surface and said second moving endless surface in said proximity point is between 0.5 mm and 30 mm.

7. The apparatus of claim 3, wherein the ratio of the radius of the cylindrical first moving endless surface, or of the first stator to the radius of the cylindrical second moving endless surface or of said second stator is 1:2 or less.

8. The apparatus of claim 1, wherein the first vacuum chamber and second vacuum chamber are connected to a same vacuum fan with a connection that comprises a gas flow regulator.

9. The apparatus of claim 1, wherein the first vacuum chamber is connected to a first vacuum fan and the second vacuum chamber is connected to a second vacuum fan.

10. The apparatus of claim 3, wherein the first vacuum chamber and second vacuum chamber are present in said second stator and said first vacuum chamber has a MD dimension defined by a first angle ($\alpha$) and said second vacuum chamber has a MD dimension defined by a second angle ($\beta$) and the ratio of $\alpha$ to $\beta$ is 2:3 or less.

* * * * *